United States Patent
Kargar et al.

(10) Patent No.: US 7,668,294 B2
(45) Date of Patent: Feb. 23, 2010

(54) METHOD AND SYSTEM FOR ADJUSTING THE IMAGE ACQUISITION SIZE IN A BIPLANE ANGIOGRAPHY

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/361,934

(22) Filed: Jan. 29, 2009

(65) Prior Publication Data

US 2009/0190717 A1    Jul. 30, 2009

Related U.S. Application Data

(60) Provisional application No. 61/024,329, filed on Jan. 29, 2008.

(51) Int. Cl.
*H05G 1/64* (2006.01)
*H05G 1/70* (2006.01)
*G06K 9/60* (2006.01)

(52) U.S. Cl. .................. 378/98.8; 378/92; 378/98; 382/130; 382/132

(58) Field of Classification Search ............. 378/62, 378/91, 92, 98, 98.2, 98.8, 204, 210; 382/128, 382/130, 132, 278, 294, 298
See application file for complete search history.

(56) References Cited

U.S. PATENT DOCUMENTS

| 2003/0016786 A1* | 1/2003 | Horbaschek ............... 378/98.8 |
| 2007/0127791 A1 | 6/2007 | Ernvik et al. |
| 2009/0016587 A1 | 1/2009 | Strobel et al. |

* cited by examiner

*Primary Examiner*—Edward J Glick
*Assistant Examiner*—Anastasia Midkiff
(74) *Attorney, Agent, or Firm*—Alexander J. Burke

(57) ABSTRACT

A system and method are disclosed for acquiring images in a biplane angiography system. The system and method allows synchronization of the image zoom format settings for the x-ray images acquired from the two planes of the biplane angiography system thus allowing the user to adjust the image zoom format setting for only one image plane.

6 Claims, 2 Drawing Sheets

METHOD AND SYSTEM FOR ADJUSTING THE IMAGE ACQUISITION SIZE IN A BIPLANE ANGIOGRAPHY

CROSS-REFERENCE TO RELATED APPLICATIONS

This is a non-provisional application of U.S. provisional patent application Ser. No. 61/024,329, filed Jan. 29, 2008, the entirety of which application is incorporated by reference herein.

FIELD OF THE DISCLOSURE

The disclosure is related to methods for acquisition of biplane angiography images.

BACKGROUND

An angiogram is a specialized x-ray examination of the blood vessels of the brain and other parts of the body. Angiography involves an injection of contrast medium to outline the blood vessels in order to render them visible in the x-ray images. The injection of the contrast medium is typically done through a small tube inserted into the groin of the patient.

Biplane angiography system features two sets of x-ray tube/x-ray detector pairs positioned at 90-degree angles allowing the blood vessels to be viewed from two different angles at the same time. Compared to the old single plane imaging equipment which gave a view of the blood vessels in only one plane, the biplane angiography system allows the physicians to locate the blood vessels more accurately through the provision of the two views.

In an angiography system, a user obtains a desired size for the image acquired by the x-ray detector by adjusting the zoom format of the x-ray images acquired on the x-ray detector. In a biplane angiography system, because there are two separate plane images acquired by the two x-ray detectors, a user needs to adjust the x-ray image zoom format for each x-ray imaging plane separately. Generally, the physicians desire to have the biplane images acquired on the same zoom sizes. This, however, requires the user to adjust the image zoom formats twice, one for each of the two x-ray detectors, and results in duplication of tasks that add undesirable time to medical procedures requiring biplane angiography.

SUMMARY OF THE DISCLOSURE

A method for acquiring images in a biplane angiography system according to an embodiment is disclosed. The biplane angiography system comprises a first pair of an x-ray source and an x-ray detector, a second pair of an x-ray source and an x-ray detector, at least one display and a system controller that is connected to and in communication with the first x-ray detector, the second x-ray detector and the at least one display. The method comprises the system controller copying image zoom format setting selected for x-ray images acquired from the first x-ray detector, upon receiving a synchronization signal, and applying the image zoom format setting to x-ray images acquired from the second x-ray detector. The result is that subsequent x-ray images acquired from the second x-ray detector have the same image zoom format as the x-ray images acquired from the first x-ray detector.

A system for acquiring images for use in a biplane angiography system comprising a first pair of an x-ray source and an x-ray detector, a second pair of an x-ray source and an x-ray detector, at least one display, a machine-readable storage medium and a system controller connected to and in communication with the first x-ray detector, the second x-ray detector, the at least one display and the machine-readable storage medium. The machine-readable storage medium is encoded with a computer program code such that, when the computer program code is executed by the system controller, the system controller performs a method comprising the system controller copying image zoom format setting selected for x-ray images acquired from the first x-ray detector, upon receiving a synchronization signal; and applying the image zoom format setting to x-ray images acquired from the second x-ray detector. The result is that subsequent x-ray images acquired from the second x-ray detector have the same image zoom format as the x-ray images acquired from the first x-ray detector.

BRIEF DESCRIPTION OF THE DRAWINGS

The accompanying drawings illustrate preferred embodiments of the disclosed method so far devised for the practical application of the principles thereof, and in which.

DETAILED DESCRIPTION

An "image zoom format" refers to one of a number of image sizes that an x-ray image being acquired from the x-ray detectors of a biplane angiography system can be formatted to. An "image zoom format setting" refers to a particular image zoom format selected from a set of a number of image zoom formats. "X-ray plane image" is an x-ray image acquired from an x-ray detector corresponding to one of the two imaging planes in a biplane angiography system.

Figure 1:
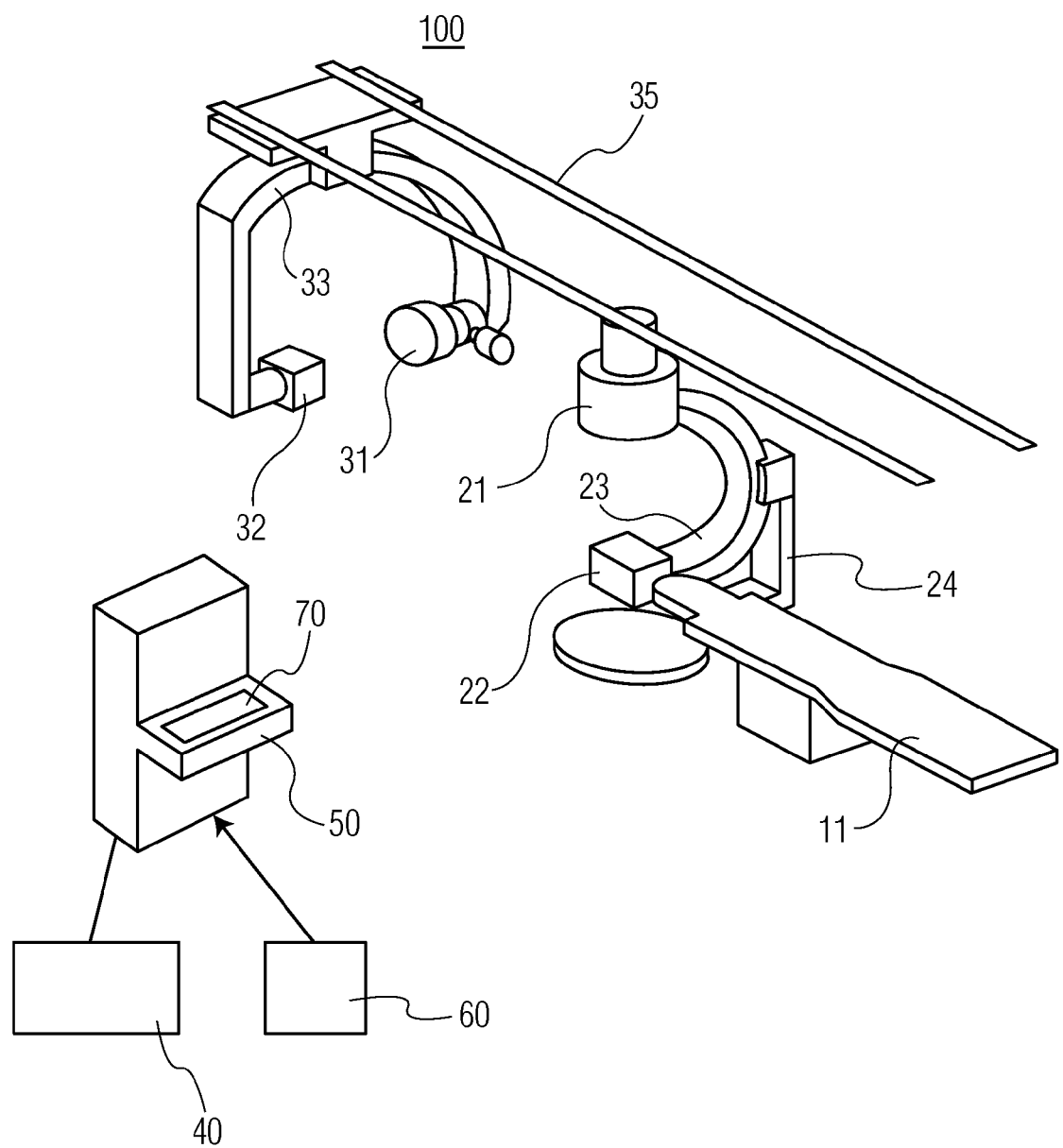
FIG. 1 is a is a schematic diagram showing a biplane angiography system in which the method and system for adjusting the x-ray image acquisition size disclosed herein is implemented.

Referring to FIG. 1, an exemplary biplane angiography system 100 is shown. The biplane angiography system 100 may comprise a first pair of an x-ray source 22 and an x-ray detector 21, a second pair of an x-ray source 32 and an x-ray detector 31, at least one display 40 and a system controller 50. The system controller 50 is connected to and in communication with the first pair of x-ray source 22 and x-ray detector 21, the second pair of x-ray source 32 and x-ray detector 31 and the at least one display 40. The first pair of x-ray source 22 and x-ray detector 21 is for acquiring x-ray images in one plane and the second pair of x-ray source 32 and x-ray detector 31 is for acquiring x-ray images in a second plane. The x-ray detectors 21, 31 can be a flat panel detector that acquires digital image frames directly, which are transferred to the system controller 50 that is appropriately configured with an image processing functionality to process the x-ray images received from the x-ray detectors 21, 31. The system controller 50 may also be configured with an x-ray image recording functionality to record the x-ray images acquired by the x-ray detectors 21, 31. The biplane angiography system 100 also includes a patient table 11 for accommodating a patient (not shown). The patient table 11 can be configured and adapted to controllably adjust the position of the patient lying on the table with respect to the rest of the angiography system 100. The first pair of x-ray source 22 and x-ray detector 21 is provided on a movable arm 23 for adjusting the angular orientation of the first pair of x-ray source and detector with respect to the patient table 11. The movable arm 23 may be mounted on a suitable base 24 and movable with respect to the patient table 11 as appropriate. The second pair of x-ray source 32 and x-ray detector 31 are provided on a second movable arm 33 for adjusting the angular orientation of the second pair x-ray source and detector with respect to the patient table 11. The second movable arm 33 may be mounted on a gantry 35 and movable with respect to the patient table 11 and the first movable arm 23.

Each of the x-ray sources 22 and 32 also includes a collimator (not shown) which is used to define the size and shape of the x-ray beam emerging from the x-ray sources 22, 32. The system controller 50 is configured to control the x-ray sources' collimator position for changing the size of the x-ray images being acquired by the respective x-ray detectors 21, 31. The system controller 50 may be a personal computer or any known controller capable of receiving and transmitting control signals to/from the above-described x-ray system components. The system controller 50 may include one or more user input devices 70, such as a trackball, mouse, joystick, buttons, switches and/or a keyboard to provide for user input in carrying out various system functions, such as mode selection, linearity control, x-ray dose control, data storage, etc. The system controller 50 may include a μ-processor executing instructions for performing one or more steps of the disclosed method.

In the biplane angiography system 100, the size of the x-ray images acquired from the two x-ray detectors 21, 31 can be changed by selecting an image zoom format setting from a predefined set of image zoom format settings. The predefined set of image zoom format settings for the acquired x-ray images are available in a number of different pixel matrix sizes such as 1024×1024, 512×512, etc. A user can select a desired image zoom format setting through the use of the one or more user input devices 70 provided on the system controller 50. Based on the image zoom format setting selected by the user for a selected x-ray imaging plane, the system controller 50 executes an appropriate software algorithm for adjusting the collimator associated with the corresponding x-ray source 22 or 32 to an appropriate collimator position. The system controller 50 adjusts that collimator's position so that it narrows the x-ray beam for zooming in on a small area in a patient's body (not shown) and broadens the x-ray beam for zooming out to a larger area in the patient's body.

According to the disclosed method, the biplane angiography system 100 allows the user to synchronize the image zoom format settings for the x-ray images acquired from the two x-ray detectors 21 and 31, one for each plane. The user can initiate or stop a synchronization command to the system controller 50 by the use of one of the one or more user input devices 70. For example, the one or more user input devices 70 may include a button that the user presses to initiate the synchronization command and presses the button again to stop the synchronization command. In another example, the one or more user input devices 70 may present the user with a graphical button on the one or more displays 40 which may be actuated by a click of a mouse.

The synchronization of the image zoom format setting results in the system controller 50 adjusting the position of the collimators associated with the x-ray sources 22 and 32 so that the images acquired from the respective x-ray detectors 21, 32 have the same matrix size. Upon receiving the synchronization command, the system controller 50 copies the image zoom format setting selected for x-ray images acquired from one of the two x-ray detectors and applies the setting to the x-ray images acquired from the other x-ray detector so that the x-ray images acquired from both x-ray detectors have the same image zoom format. Subsequent adjustment or change to the image zoom format setting for x-ray images acquired from either of the two x-ray detectors 21, 31 is applied to the x-ray images acquired from the other of the two x-ray detectors so that their image zoom formats are adjusted concurrently.

In one embodiment, the user can initiate the synchronization command first and then adjust the image zoom format setting for the desired x-ray plane image. In that case, the system controller 50 copies the image zoom format setting from one of the image zoom format setting to the other x-ray plane image so that the two x-ray plane images have the same image zoom format setting. Subsequent adjustment or selection of new image zoom format for one of the two x-ray plane images is copied and applied to the other x-ray plane image.

In another embodiment, the user adjusts or selects the image zoom format setting for one of the two x-ray plane images first. When a synchronization command is subsequently initiated by the user, the system controller 50 copies the image zoom format setting selected by the user for the first x-ray plane image and automatically applies it to the other x-ray plane image. Until the user stops the synchronization command by unselecting the synchronization through the one or more user interface devices 70, subsequent adjustment or selection of new image zoom format setting for one of the two x-ray plane images is applied to the other x-ray plane image.

In either case, the result is that the system controller 50 automatically synchronizes the image zoom format settings for the x-ray images acquired from the two x-ray detectors 21, 32 and relieves the user from having to separately adjust the image zoom format settings for each of the x-ray plane images.

Figure 2:
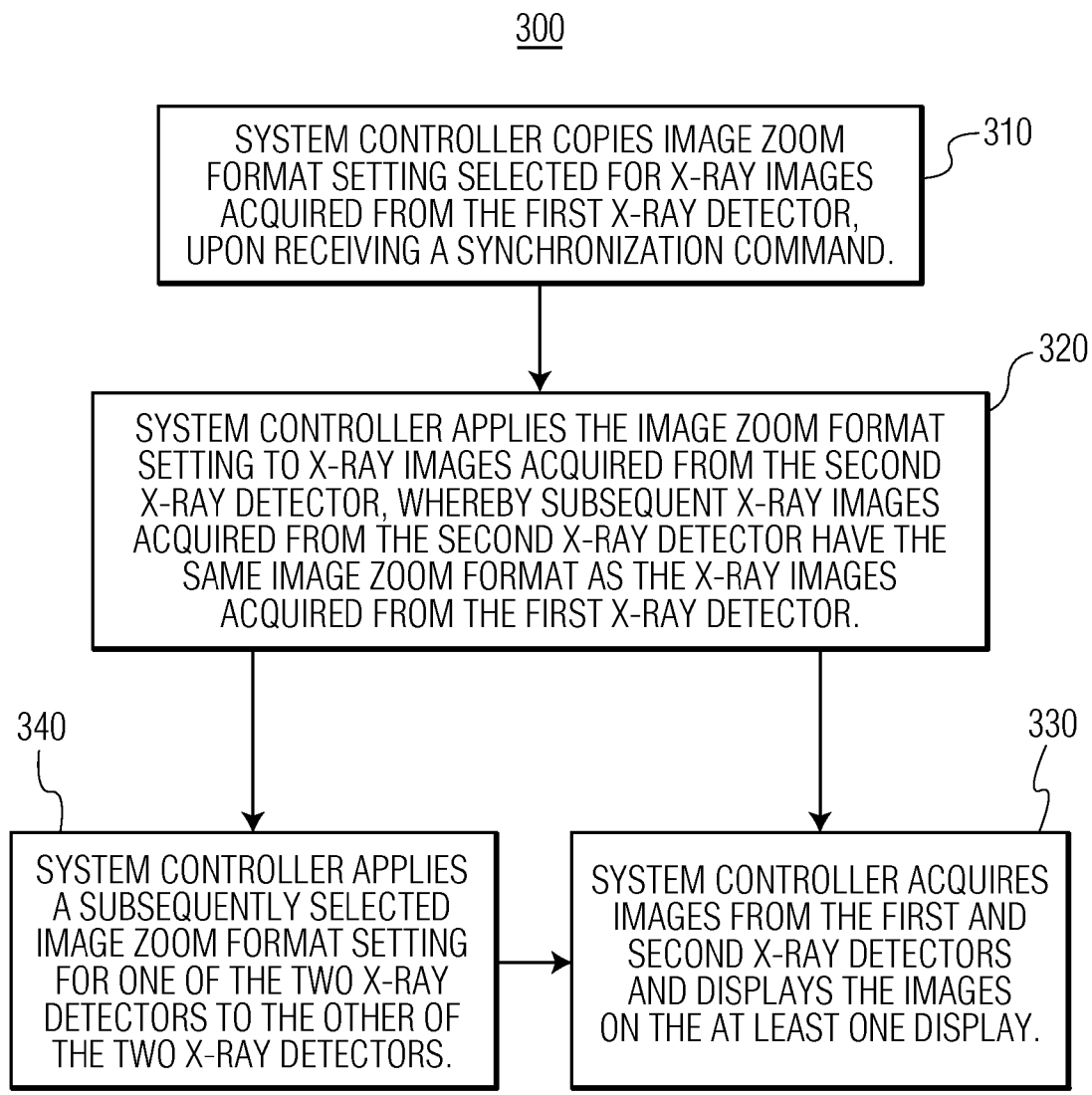
FIG. 2 is a flow chart describing a sequence of steps of the disclosed method.

Referring to FIG. 2, the disclosed method will be described in greater detail. At step 310, the system controller 50 copies the image zoom format setting selected for x-ray images acquired from the first x-ray detector 21, upon receiving a synchronization signal. The image zoom format setting information can be copied into a suitable memory storage available to the system controller. At step 320, the system controller 50 applies that same image zoom format setting to x-ray images acquired from the second x-ray detector 31. Applying the image zoom format setting to the second x-ray detector 31 comprises the system controller 50 controlling the collimator associated with the second x-ray source 32 to a position corresponding to the particular image zoom format setting. The result is that x-ray images acquired from the second x-ray detector 31 has the same zoom format as the x-ray images acquired from the first x-ray detector 21, thus, eliminating the need for the user to separately adjust the zoom format setting for the second x-ray detector 31. At step 330, the system controller 50 acquires x-ray images from the first and second x-ray detectors and displays the x-ray images on the at least one display 40. The two x-ray images from the two x-ray detectors 21, 31 may be displayed side-by-side on a single display or they may be displayed on two individual displays as appropriate.

If the subsequent operation of the biplane angiography system 100 requires, at step 340, the system controller 50 applies a subsequently selected image zoom format setting for x-ray images acquired from one of the two x-ray detectors 21, 31 to the other of the two-x-ray detectors. In other words, after the initial synchronization of the image zoom formats for the x-ray images acquired from the first and second x-ray detectors are achieved (see steps 310 and 320), if the user adjusts or changes the image zoom format for x-ray images acquired from one of the two x-ray detectors 21, 31 corresponding to a desired image plane in order to perform another procedure, the system controller 50 will apply the subsequently selected image zoom format setting to the other x-ray detector. Again, the system controller 50 can acquire x-ray images from the first and second x-ray detectors and display the two plane images on the at least one display 40.

The method described herein may be automated by, for example, tangibly embodying a program of instructions upon a machine-readable storage media 60 capable of being read by a machine, such as the system controller 50, capable of executing the instructions. A general purpose computer is one example of such a machine. A non-limiting exemplary list of appropriate storage media well known in the art would include such devices as a read-only-memory or a magnetic storage disk provided in the system controller 50, for example. The machine-readable storage media 60 can be a portable device such as a readable or writeable CD, flash memory chips (e.g., thumb drives), various magnetic storage media, and the like.

The features of the method have been disclosed, and further variations will be apparent to persons skilled in the art. All such variations are considered to be within the scope of the appended claims. Reference should be made to the appended claims, rather than the foregoing specification, as indicating the true scope of the disclosed method.

The functions and process steps herein may be performed automatically or wholly or partially in response to user command. An activity (including a step) performed automatically is performed in response to executable instruction or device operation without user direct initiation of the activity.

The systems and processes illustrated and discussed herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIG. 1. Further, any of the functions and steps provided in FIG. 2 may be implemented in hardware, software or a combination of both and may reside on one or more processing devices located at any location of a network linking the elements of FIG. 1 or another linked network, including the Internet.

We claim:

1. A method for acquiring images in a biplane angiography system comprising a first pair of an x-ray source and an x-ray detector, a second pair of an x-ray source and an x-ray detector, at least one display and a system controller connected to and in communication with the first pair of an x-ray source and x-ray detector, the second pair of an x-ray source and an x-ray detector and the at least one display, the method comprising:

the system controller copying image zoom format setting selected for x-ray images acquired from the first x-ray detector, upon receiving a synchronization command; and applying the image zoom format setting to x-ray images acquired from the second x-ray detector so subsequent x-ray images acquired from the second x-ray detector have the same image zoom format as the x-ray images acquired from the first x-ray detector.

2. The method of claim 1, further comprising the system controller acquiring x-ray images from the first and second x-ray detectors and displaying the x-ray images on the at least one display.

3. The method of claim 1, further comprising the system controller applying a subsequently selected image zoom format setting for x-ray images acquired from one of the two x-ray detectors to the other of the two x-ray detectors.

4. A system for acquiring images for use in a biplane angiography system comprising a first pair of an x-ray source and an x-ray detector, a second pair of an x-ray source and an x-ray detector, at least one display, a machine-readable storage medium and a system controller connected to and in communication with the first x-ray detector, the second x-ray detector, the at least one display and the machine-readable storage medium, wherein the machine-readable storage medium being encoded with a computer program code such that, when the computer program code is executed by the system controller, the system controller performs a method comprising:

copying image zoom format setting selected for x-ray images acquired from the first x-ray detector, upon receiving a synchronization command; and applying the image zoom format setting to x-ray images acquired from the second x-ray detector so subsequent x-ray images acquired from the second x-ray detector have the same image zoom format as the x-ray images acquired from the first x-ray detector.

5. The system of claim 4, wherein the method performed by the system controller further comprises the system controller acquiring x-ray images from the first and second x-ray detectors and displaying the x-ray images on the at least one display.

6. The system of claim 4, wherein the method performed by the system controller further comprises the system controller applying a subsequently selected image zoom format setting for x-ray images acquired from one of the two x-ray detectors to the other of the two x-ray detectors.

* * * * *